United States Patent [19]

Esvan et al.

[11] Patent Number: 5,181,415
[45] Date of Patent: Jan. 26, 1993

[54] APPARATUS FOR DETECTING A CHANGE OF VISCOSITY BY MEASURING A RELATIVE SLIP, IN PARTICULAR FOR DETECTING THE COAGULATION RATE OF BLOOD

[75] Inventors: Daniel Esvan, Maffliers; Jean P. Roisin, Saint Maur des Fosses, both of France

[73] Assignee: Serbio, France

[21] Appl. No.: 732,388

[22] Filed: Jul. 18, 1991

[30] Foreign Application Priority Data

Jul. 20, 1990 [FR] France ................. 90 09284

[51] Int. Cl.⁵ .................. G01N 11/14; G01N 33/49
[52] U.S. Cl. ..................... 73/54.28; 73/64.41; 436/69
[58] Field of Search ......... 73/64.1, 59; 422/73; 436/69

[56] References Cited

U.S. PATENT DOCUMENTS

| | | | |
|---|---|---|---|
| 3,053,078 | 9/1962 | Jewett | 73/59 X |
| 3,667,286 | 6/1972 | Kaufman et al. | 73/59 |
| 4,202,204 | 5/1980 | Hartert | 73/64.1 |
| 5,072,610 | 12/1991 | Martinoli et al. | 73/64.1 |

Primary Examiner—Hezron E. Williams
Assistant Examiner—Joseph W. Roskos
Attorney, Agent, or Firm—William A. Drucker

[57] ABSTRACT

An apparatus is disclosed for detecting a change of viscosity of a blood sample in time, comprising a drive element and a driven element having respective facing walls which define therebetween a chamber of calibrated volume adapted to receive a blood sample, the driven element being driven in relative rotation by the drive element with a relative slip which depends on the viscosity of the blood which provides coupling between the two elements and means for measuring the relative change of slip.

7 Claims, 1 Drawing Sheet

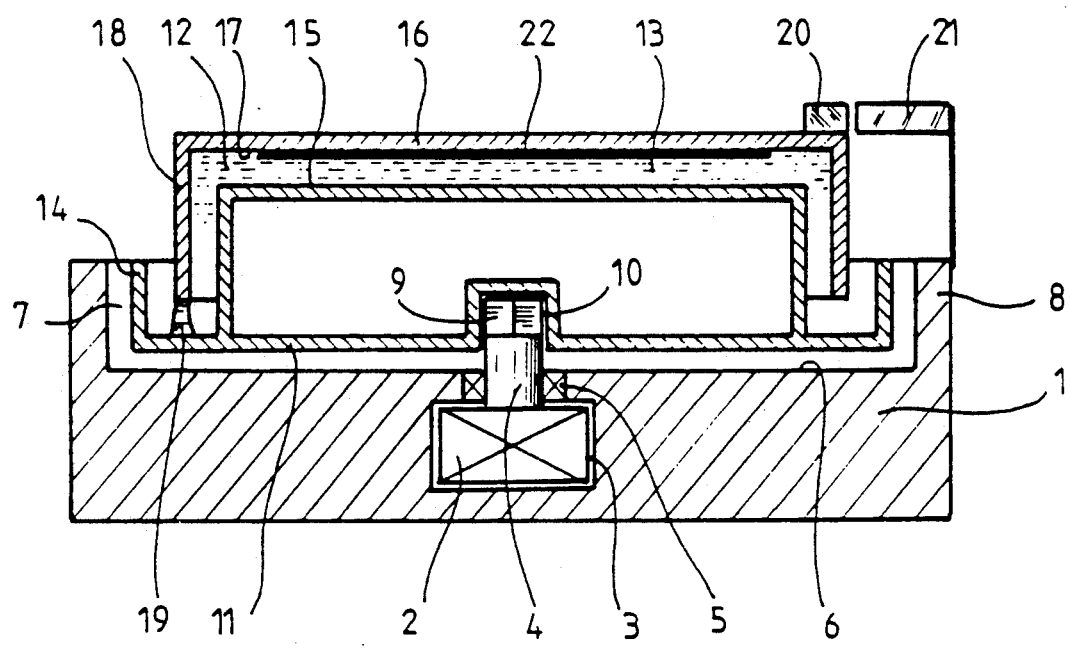

APPARATUS FOR DETECTING A CHANGE OF VISCOSITY BY MEASURING A RELATIVE SLIP, IN PARTICULAR FOR DETECTING THE COAGULATION RATE OF BLOOD

BACKGROUND OF THE INVENTION

The present invention relates to an apparatus for detecting a change of viscosity of a fluid medium in time.

More particularly, it is designed to measure the coagulation rate of a blood sample in contact with an appropriate reagent.

Numerous solutions have been proposed for measuring the coagulation rate of blood plasma, such for example as introducing a ferromagnetic ball into the bottom of a cup, containing the plasma to be tested, which is driven with a periodic movement under the effect of an external magnetic field and in which the modifications of the movements of this ball, due to the coagulation, are detected.

Such devices require the use of centrifuged blood or plasma introduced in an appreciable quantity in a cup. Moreover, the reagents used are lyophilized and must be reconstituted with distilled water at the time of use.

SUMMARY OF THE INVENTION

The aim of the present invention is to overcome this drawback by providing an apparatus for ambulatory use, for the personal use of patients under supervision, who must carry out frequent tests, without using complicated, cumbersome equipment requiring to be sterilized after use.

According to a characteristic of the invention, the detection apparatus comprises a drive element and a driven element having respective facing walls which define therebetween a chamber of calibrated volume adapted to receive a fluid sample, the driven element being driven in rotation with respect to the drive element with a relative slip which depends on the viscosity of the fluid which provides coupling between the two elements and means for measuring the relative slip.

Such an apparatus, designed to measure the coagulation rate of a blood sample in contact with an appropriate reagent, is also characterized in that said reagent is deposited in the form of a uniform layer on at least one of the facing walls of the drive and driven elements.

According to another characteristic of the invention, said measuring means comprise a permanent magnet cooperating with a block of magnetic material for immobilizing the driven element until the moment when the coagulation causes the facing walls to adhere together with sufficient force to cause said element to be driven.

According to another characteristic of the invention, a disposable assembly for use as element of the apparatus, comprises a drive element and a driven element formed by two plastic material parts, removable with respect to each other and adapted to define therebetween a predetermined volume corresponding substantially to that of a drop of blood, the drive element being adapted for being removably coupled to drive members which the apparatus comprises.

BRIEF DESCRIPTION OF THE DRAWING

The invention will be further illustrated without being in any wise limited by the following description, with reference to the accompanying drawing in which:

The single figure is a schematic sectional view of an apparatus for measuring the coagulation rate of blood, according to the invention.

DESCRIPTION OF THE PREFERRED EMBODIMENT

The apparatus shown in the single figure comprises a frame 1 containing an electric motor 2 inserted vertically in a housing 3 and whose vertical shaft 4 is directed upwards and is journalled in a bearing 5 of frame 1. Shaft 4 passes through the bottom 6 of frame 1 and emerges into a housing 7 formed by a peripheral side wall 8 in connection with said bottom 6.

The shaft 4 of motor 2 comprises, at its free end emerging into housing 7, a driving square 9 adapted to be housed in a corresponding blind square 10 formed coaxially with the lower part of a first element 11 for securing it to shaft 4 and thus making it possible to rotate it by means of motor 2. Said first element 11 thus secured to the drive shaft will consequently afterwards be called the drive element 11.

The drive element 11 comprises at its upper part a flat wall 15 defining, with an internal wall 17 of a facing driven element 16, a chamber 12 of calibrated volume adapted to receive a drop of blood 13.

The drive element 11 comprises at its lower part a peripheral flange 14 forming an annular groove adapted to recover the excess blood 13.

The drive element 11 is capped without any mechanical stress by the driven element 16 close to its upper end formed by plane 15.

The driven element 16 forms an upturned cup-shaped lid whose bottom forms wall 17 which defines said chamber 12 with the flat wall 15 of the drive element 11.

The driven element 16 comprises an axial peripheral flange 18 which is housed with play in groove 14 of the drive element 11 so as to form a baffle.

An electric closure contact 19, formed for example by a wiper, is inserted between the end of flange 18 of the driven element 16 and the bottom of groove 14 of the drive element 11 forming a baffle therebetween.

The driven element 16 comprises, close to its external periphery, a block 20 cooperating with a permanent magnet 21 secured to a fixed part of frame 1, by any known fixing means.

In this present example, a reagent 22 is deposited in the form of a layer on the internal wall 17 of the driven element 16 but, of course, it could be deposited on the wall 15 of the drive element 11 or else, at one and the same time, on walls 15, 17 of the two elements.

The reagent 22 is deposited with a constant surface density so as to obtain an action on the blood which is balanced over the whole contact area.

In order to facilitate its spreading over wall 17, it may be mixed with a gel which is then dried.

The operation of such an apparatus will be described hereafter.

A drop of blood 13 is deposited on the flat wall 15 of the drive element 11 on which it spreads out, then is covered by the driven element 16 forming a closure lid. Thus, the fluid sample 13 is inserted between walls 15, 17 of the drive and driven elements 11 and 16 and any excess blood is discharged towards the peripheral groove 14 of the drive element 11.

When the motor is started up, the shaft 4 meshing at its square end 9 with the drive element 11, as described above, drives this latter with a predetermined speed of rotation.

Initially, the driven element 16 is immobilized by the magnetic force of attraction of the permanent magnet 21 acting on the magnetic material block 20 fixed to said element 16 and thus preventing it from rotating, a sufficient relative slip then existing between walls 15, 17 via the blood 13 which is fluid at this stage.

In addition, when the driven element 16 is positioned initially to cap the drive element 11, an electric circuit is formed through the closure contact 19 forming part of a generator circuit, not shown but known per se, delivering a blip for starting the measurement of the time by any appropriate means.

The action of the reagent 22 on blood 13 will be progressive during the measurement and the driven element will remain motionless as long as its relative slip with respect to the drive element 11 is of a value less than the magnetic force of attraction formed between block 20 and magnet 21.

Under the action and as a function of reagent 22, the blood coagulates in a variable time, to be measured, and causes walls 15, 17 to adhere together, thus interlocking the driven element 16 for rotation with the drive element 11 with sufficient force. Cutting off the magnetic field between block 20 and magnet 21 causes a blip at the end of the measurement of the time which is taken into account by said appropriate means.

At the end of the measurement of the coagulation rate of the blood to be tested, the drive element 11 and the driven element 16 form a disposable assembly. Preferably, these elements are made from a plastic material.

After such measurement and after throwing away the elements 11, 16, the apparatus is available for a new test by disposing a new apparatus therein.

It can be seen that the apparatus according to the invention advantageously forms an ambulatory assembly, which is independent and which avoids any risk of contamination because of the complete elimination of the elements having been in contact with the blood to be tested.

What is claimed is:

1. An apparatus for detecting a change of viscosity of a fluid medium in time, comprising a drive element and a driven element having respective facing walls which define therebetween a chamber of calibrated volume adapted to receive a fluid sample, the driven element being driven in relative rotation by the drive element with a relative slip which depends on the viscosity of the fluid which provides coupling between the two elements and means for measuring the relative change of slip, wherein said measuring means comprise a magnetic means cooperating with a block of magnetic material for immobilizing the driven element until the moment when the coagulation causes the facing walls to adhere together with sufficient force to cause said driven element to be driven.

2. The apparatus as claimed in claim 1, comprising means for determining the time when the relative slip becomes less than a predetermined threshold.

3. The apparatus as claimed in claim 1 for measuring the coagulation rate of a blood sample in contact with an appropriate reagent, wherein said reagent is deposited in the form of a uniform layer on at least one of the facing walls of the drive and driven elements.

4. The apparatus as claimed in claim 1, wherein the driven element forms a lid which caps the drive element, the arrangement being such that a possible excess of liquid with respect to the calibrated volume is driven outside.

5. The apparatus as claimed in claim 1, wherein said elements are removable with respect to each other and an electric contact is formed at a moment when they are placed in a position which defines a predetermined volume, said electric contact forming part of a circuit generating a blip for starting a time measurement, means for detecting a beginning of driving of the driven element delivering a blip when the time measurement is ended.

6. The apparatus as claimed in claim 1, wherein said magnetic element is a permanent magnet.

7. The apparatus as claimed in claim 1, wherein said drive element forms with the driven element a disposable assembly which is removably assembled to said apparatus.

* * * * *